(12) United States Patent
Castro-Perdomo et al.

(10) Patent No.: US 10,172,688 B2
(45) Date of Patent: Jan. 8, 2019

(54) STEAM CLEANING DEVICE AND METHODS OF USE

(71) Applicants: Carlos Andres Castro-Perdomo, Atlanta, GA (US); Carlos Ariel Castro-Saenz, Lilburn, GA (US)

(72) Inventors: Carlos Andres Castro-Perdomo, Atlanta, GA (US); Carlos Ariel Castro-Saenz, Lilburn, GA (US)

( * ) Notice: Subject to any disclaimer, the term of this patent is extended or adjusted under 35 U.S.C. 154(b) by 100 days.

(21) Appl. No.: 15/133,626

(22) Filed: Apr. 20, 2016

(65) Prior Publication Data
US 2016/0374777 A1 Dec. 29, 2016

Related U.S. Application Data

(60) Provisional application No. 62/183,895, filed on Jun. 24, 2015.

(51) Int. Cl.
*A61C 1/00* (2006.01)
*A61C 17/02* (2006.01)
(Continued)

(52) U.S. Cl.
CPC .......... *A61C 1/0061* (2013.01); *A61C 1/0069* (2013.01); *A61C 8/00* (2013.01);
(Continued)

(58) Field of Classification Search
CPC ... A61C 1/0061; A61C 1/0069; A61C 1/0076; A61C 1/0092; A61C 1/0084;
(Continued)

(56) References Cited

U.S. PATENT DOCUMENTS

| 3,753,435 A | * | 8/1973 | Blasnik | A61H 13/005 |
| | | | | 601/163 |
| 4,034,203 A | * | 7/1977 | Cooper | B60S 3/04 |
| | | | | 137/341 |

(Continued)

OTHER PUBLICATIONS

Kim, et al., "Decontamination methods for micro-threaded implant fixtures using a dental water jet and dental floss," Clinical Oral Implants Research, vol. 25, suppl. 10, 2014, pp. 380-381.

(Continued)

*Primary Examiner* — Nicholas Lucchesi
*Assistant Examiner* — Shannel Wright
(74) *Attorney, Agent, or Firm* — Meunier Carlin & Curfman LLC

(57) ABSTRACT

According to various implementations, a dental cleaning device includes a steam conduit and a cooling fluid conduit. The steam conduit has a distal tip with an opening defined therein that allows steam to be applied intraorally close to a dental implant to flush away bacteria that has colonized on or adjacent the dental implant. The cooling fluid conduit has a distal tip with an opening defined therein that allows a cooling fluid to be applied intraorally close to the dental implant following the application of the steam to cool the tissue and prevent overheating of the tissue and bone adjacent the dental implant. For example, the cooling fluid may be applied intermittently with the steam, or the cooling fluid may be applied continuously while the steam is applied intermittently, according to various implementations.

12 Claims, 3 Drawing Sheets

(51) Int. Cl.
*A61C 8/00* (2006.01)
*A61C 19/06* (2006.01)
*A61M 35/00* (2006.01)
*B08B 3/02* (2006.01)

(52) U.S. Cl.
CPC .......... *A61C 17/02* (2013.01); *A61C 17/0202* (2013.01); *A61C 19/06* (2013.01); *A61M 35/00* (2013.01); *B08B 3/026* (2013.01); *B08B 2230/01* (2013.01)

(58) Field of Classification Search
CPC ... A61C 17/02; A61C 17/0202; A61C 17/022; A61C 17/028; A61C 19/06
See application file for complete search history.

(56) References Cited

U.S. PATENT DOCUMENTS

| | | | | |
|---|---|---|---|---|
| 4,249,899 A | * | 2/1981 | Davis | A61C 17/0217 222/146.5 |
| 4,299,221 A | * | 11/1981 | Phillips | A61C 17/04 433/100 |
| 5,076,467 A | * | 12/1991 | Sugo | A61C 13/12 222/146.5 |
| 7,011,644 B1 | * | 3/2006 | Andrew | A61C 17/0208 433/215 |
| 7,059,853 B2 | * | 6/2006 | Hegemann | A61C 1/0092 132/322 |
| 8,573,974 B2 | * | 11/2013 | Janssen | A61C 17/0217 433/88 |
| 2001/0004695 A1 | * | 6/2001 | Vercellotti | A61B 17/1688 606/79 |
| 2002/0102182 A1 | * | 8/2002 | Suddath | A61C 1/0076 422/26 |
| 2003/0232302 A1 | * | 12/2003 | Babayoff | A61B 1/253 433/29 |
| 2009/0010825 A1 | * | 1/2009 | Polti | A61L 2/07 422/298 |
| 2009/0130622 A1 | * | 5/2009 | Bollinger | A61C 1/0046 433/29 |
| 2011/0183284 A1 | * | 7/2011 | Yamanaka | A61C 17/02 433/32 |
| 2013/0177869 A1 | * | 7/2013 | Black | A61C 17/16 433/89 |
| 2014/0147804 A1 | * | 5/2014 | Yamamoto | A61C 17/20 433/29 |
| 2014/0342308 A1 | * | 11/2014 | Weathers | A61C 3/025 433/88 |
| 2015/0010882 A1 | * | 1/2015 | Bergheim | A61C 17/02 433/80 |
| 2015/0150649 A1 | * | 6/2015 | Dresser | A61C 1/0084 433/31 |
| 2015/0188023 A1 | * | 7/2015 | Pond | A61C 1/07 433/86 |
| 2015/0297317 A1 | * | 10/2015 | Chen | A61C 1/0084 433/32 |

OTHER PUBLICATIONS

Watanabe et al., Cleaning Technique Using High-Speed Steam-Water Mixed Spray, Solid State Phenomena, vols. 145-146, pp. 43-46, 2009.

* cited by examiner

STEAM CLEANING DEVICE AND METHODS OF USE

CROSS REFERENCE TO RELATED APPLICATION

This application claims priority to U.S. Provisional Patent Application No. 62/183,895, entitled "Steam Cleaning Device and Methods of Use," and filed Jun. 24, 2015, the content of which is herein incorporated by reference in its entirety.

BACKGROUND OF INVENTION

Peri-implantitis is an inflammation of the tissue surrounding a dental implant. It also results in rapid bone loss adjacent the site of inflammation. Peri-implantitis is caused by a colonization of bacteria and their associated byproducts on or near the implant surface.

Current methods of treating peri-implantatis include using mechanical methods to flatten, smooth, or clean the contaminated implant surface (e.g., rotary instruments in implantoplasty, an air powder abrasive, an ultrasonic scaler, metallic or non-metallic curettes, or rubber cups with pumice) and chemical methods to reduce bacteria colonies (e.g., applying citric acid, chlorhexidine, hydrogen peroxide, lasers, or photodynamic therapy). Another method includes irrigation of the infected site with a saline water solution using a water jet in combination with flossing the site. However, the success rate of treating peri-implantitis using these methods is around 50%.

Furthermore, changing implant surface characteristics alters the affinity of the surface to accept growing tissues around them. Ideal cleaning of implant surfaces requires no mechanical damage of the surface and roughness required for osseointegration.

Accordingly, improved systems and methods are needed for the treatment of peri-implantitis.

BRIEF SUMMARY

A dental cleaning device and method of use are described herein. The dental cleaning device includes a hand piece which has a steam conduit and a cooling fluid conduit. The steam conduit has a distal tip with an opening defined therein that allows steam to be applied intraorally close to a dental implant (e.g., within about 0.5 and about 5 mm from the dental implant) to flush away bacteria that has colonized on or adjacent the dental implant. For example, the steam may be pressurized to between about 40 and about 80 psi, according to some implementations. The cooling fluid conduit has a distal tip with an opening defined therein that allows a cooling fluid, such as a saline water solution, to be applied intraorally close to the dental implant following the application of the steam to cool the tissue and prevent overheating of the tissue and bone adjacent the dental implant. The cooling fluid distal tip may be disposed adjacent the steam distal tip. For example, the cooling fluid may be applied intermittently with the steam (e.g., alternately apply steam for a preset time period and the cooling fluid for a preset time period), or the cooling fluid may be applied continuously while the steam is applied intermittently, according to various implementations.

For example, various implementations of a dental cleaning device include a first conduit having a first distal tip with a first opening defined therein and a second conduit having a second distal tip with a second opening defined therein. The first conduit is configured for delivering steam through the first opening intraorally. The second conduit is configured for delivering the cooling fluid through the second opening intraorally. The second opening is disposed adjacent the first opening. The device also includes a valve in fluid communication with the first conduit that is configured for selectively allowing steam to pass to the first opening. In some implementations, the valve is opened and closed intermittently. In addition, in some implementations, the dental cleaning device also includes a hand piece onto which the first and second distal tips are disposed. For example, the first and second distal tips may be configured for being removably secured to the hand piece.

In some implementations, the cooling fluid is applied intraorally after application of the steam to prevent the steam from cooking the patient's gum tissue. For example, the cooling fluid may have a temperature of about 98.6° F. or less.

In certain implementations, the first opening is sized such that a width of the steam exiting the first opening is within about 1 millimeter of a diameter of the dental implant that is being cleaned intraorally with the dental cleaning device. For example, the first opening may be between about 0.1 and about 1.5 mm in diameter. In addition, during application of the steam, the first opening may be disposed between about 0.5 and about 5 mm away from the implant surface being cleaned. The first and second openings may be defined at the end of the distal tips or on the side surfaces thereof. And, the openings may have the same or differently sized and shaped openings, such as circular, oval, triangular, rectangular, diamond, or other suitable shape.

In some implementations, the valve is a solenoid valve. The solenoid valve is in electrical communication with a computer processor that is configured for instructing the solenoid valve to open or close. In addition, the computer processor may be further configured for: (1) receiving a first input requesting that the solenoid valve be opened; (2) causing the solenoid valve to open in response to receiving the first input; (3) receiving a second input requesting that the solenoid valve be closed; and (4) causing the solenoid valve to close in response to receiving the second input.

The first input may be a signal resulting from the depression of a button on a handle to which the first and second conduit are attached, according to one implementation. Alternatively, the first input may be a signal resulting from the depression of a pedal. And in another alternative, the first input may be a signal resulting from a timer that is part of the computer processor, and the computer processor is configured for generating instructions for the solenoid valve to close after steam has passed through the first opening for a preset time period. In another alternative implementation, the timer may be separate from the computer processor but in electrical communication therewith.

In certain implementations, the flow of the cooling fluid through the second conduit is controlled by a peristaltic pump in electrical communication with the computer processor. In such implementations, the computer processor is further configured for: (1) increasing a speed of the peristaltic pump to cause the cooling fluid to flow through the distal end of the second conduit immediately after the solenoid valve has closed, and (2) decreasing the speed of the peristaltic pump to cease the cooling fluid from flowing through the distal end of the second conduit after the cooling fluid has passed through the second opening for a second preset time period. In other implementations, the computer processor may be configured for: (1) increasing a speed of the peristaltic pump to cause the cooling fluid to flow through the second opening of the second conduit immediately after the solenoid valve has closed, and (2) decreasing the speed of the peristaltic pump to cease the cooling fluid from flowing through the second opening of the second conduit immediately before the solenoid valve is opened. In other implementations, the flow of cooling fluid may be controlled by a valve or other suitable mechanism.

BRIEF DESCRIPTION OF THE DRAWINGS

The device is explained in even greater detail in the following exemplary drawings. The drawings are merely exemplary to illustrate the structure of preferred devices and certain features that may be used singularly or in combination with other features. The invention should not be limited to the implementations shown.

DETAILED DESCRIPTION

According to various implementations, a dental cleaning device includes a steam conduit and a cooling fluid conduit. The steam conduit has a distal tip with an opening defined therein that allows steam to be applied intraorally close to a dental implant to flush away bacteria that has colonized on or adjacent the dental implant. The cooling fluid conduit has a distal tip with an opening defined therein that allows a cooling fluid to be applied intraorally close to the dental implant following the application of the steam to cool the tissue and prevent overheating of the tissue and bone adjacent the dental implant. For example, the cooling fluid may be applied intermittently with the steam, or the cooling fluid may be applied continuously while the steam is applied intermittently, according to various implementations. This dental cleaning device allows cleaning of implant surfaces without damaging the surfaces, which improves the chances for reintegration.

Figure 1:
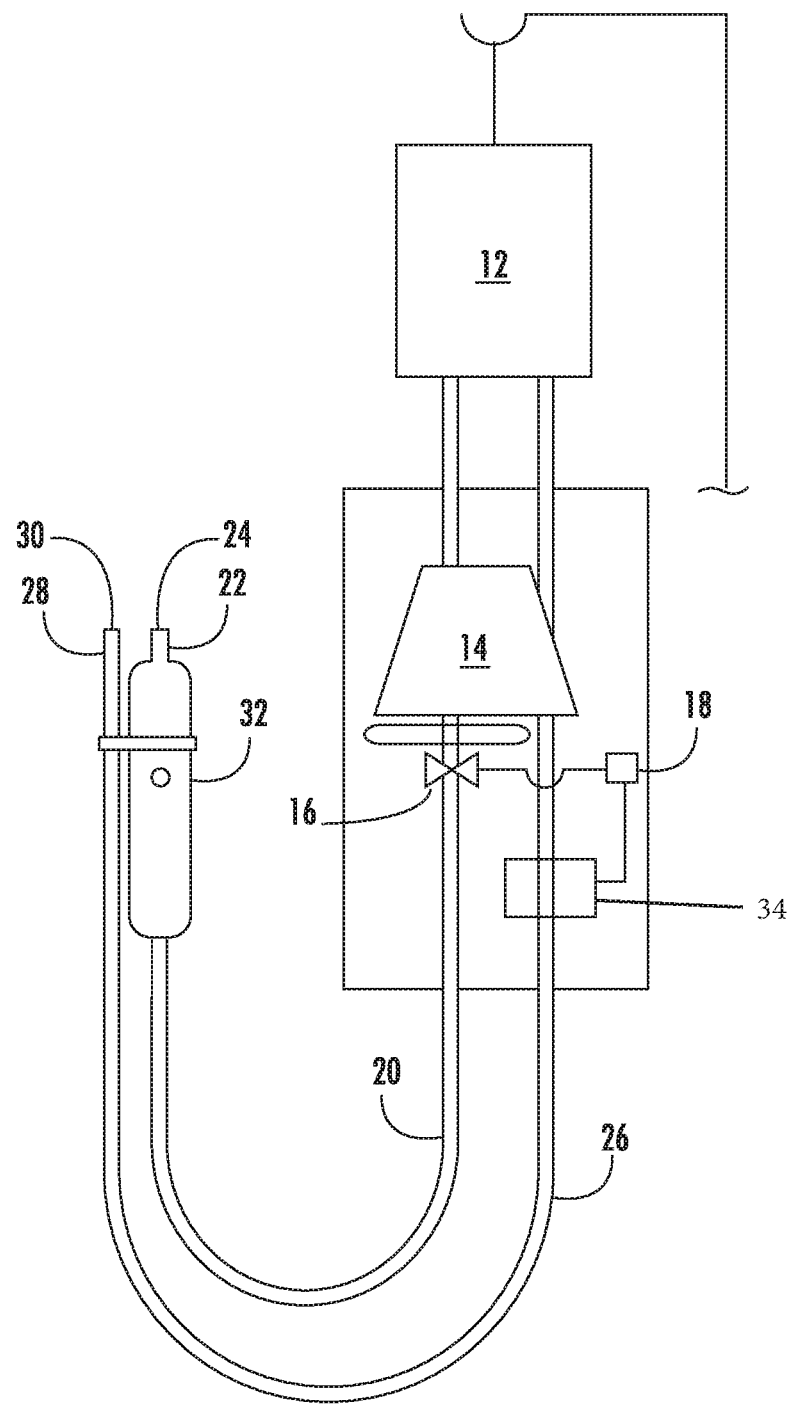
FIG. 1 illustrates a schematic view of a dental cleaning device system according to one implementation.

FIG. 1 illustrates a dental cleaning device according to one implementation. The dental cleaning device 10 includes a cooling fluid reservoir 12, a steamer 14, a solenoid valve 16, a computer processor 18, a steam conduit 20 having a distal tip 22 with an opening 24 defined therein, and a cooling fluid conduit 26 having a distal tip 28 with an opening 30 defined therein. The steam conduit 20 extends from the distal tip 22 and the solenoid valve 16, and the solenoid valve 16 is in fluid communication with the steamer 14. The steam conduit 20 is configured for delivering steam through the opening 24. The cooling fluid conduit 26 extends between the distal tip 28 and a peristaltic pump 34, and the peristaltic pump 34 is in fluid communication with the cooling fluid reservoir 12. The cooling fluid conduit 26 is configured for delivering the cooling fluid through the opening 30.

The distal tips 22, 28 are disposed adjacent each other on a hand piece 32. For example, in the implementation shown in FIG. 1, a portion of the steam conduit 20 is disposed within the hand piece 32 and a portion of the cooling fluid conduit 26 is disposed along an outer surface of the hand piece 32. In another implementation (not shown), the portion of the cooling fluid conduit 26 also may be disposed within the hand piece 32. In both implementations, the distal tips 22, 28 are disposed adjacent each other and a distal end of the hand piece 32. This arrangement of the distal tips 22, 28 allows the cooling fluid to be applied to the portion of the implant surface and the patient's tissue to which the steam is applied to prevent the steam from over-heating the patient's tissue and bone.

Figure 2A:
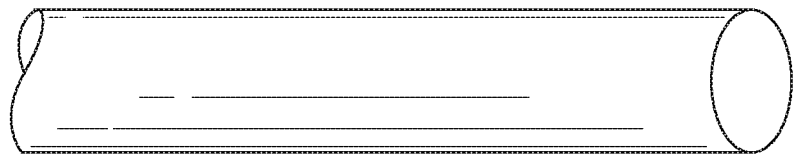
FIG. 2A through 2C illustrates distal tips of steam conduits according to various implementations.
Figure 2B:
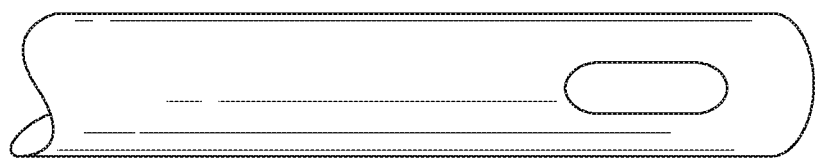
Figure 2C:
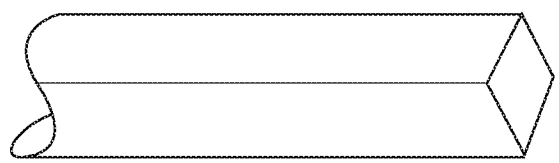
Figure 3:
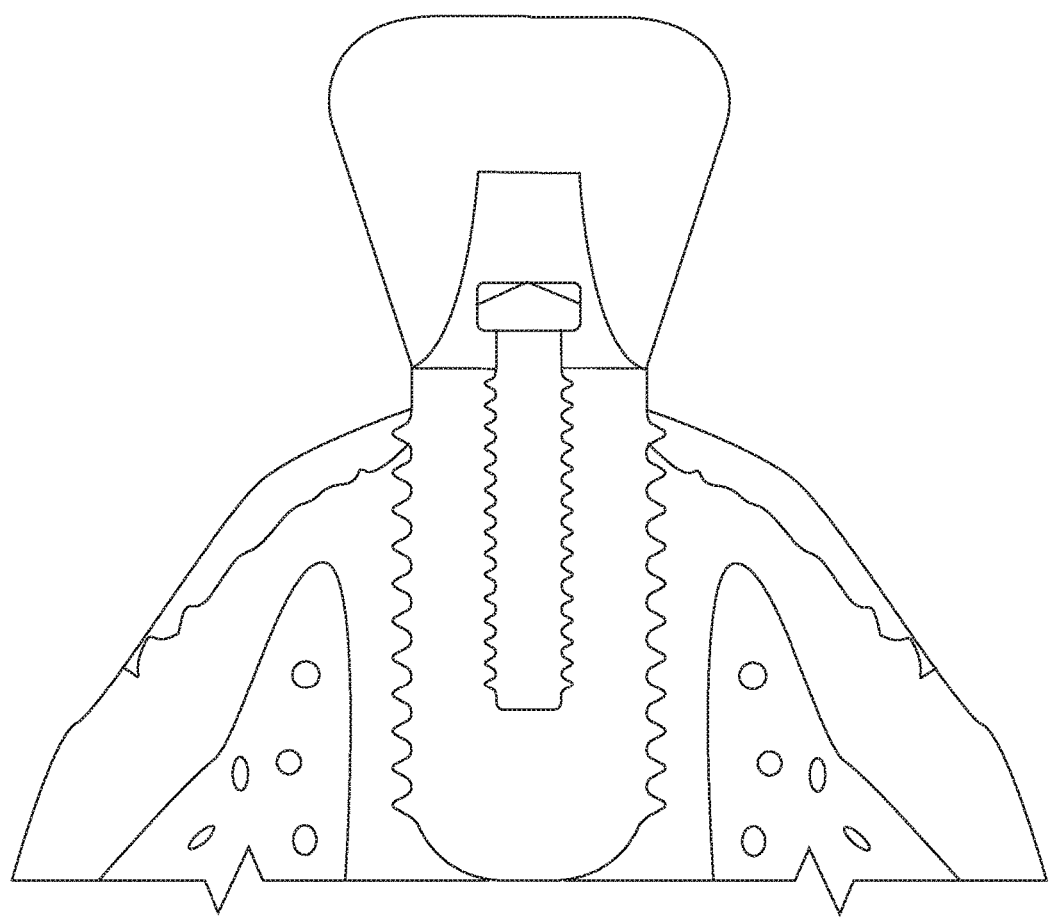
FIG. 3 illustrates a cut-away side view of a dental implant within gum tissue according to one implementation.

In some implementations, the steam distal tip 24 and the cooling fluid distal tip 28 may be removably secured to the hand piece 32. The distal tips 24, 28 may be removed for cleaning/sterilization or to change the size and/or shape of the distal tips depending on the application. Various sized and shaped distal tips are shown in FIGS. 2A-2C, but other suitable shapes and sizes are within the scope of this invention.

The steam opening 24 and the cooling fluid opening 30 may be defined at the end of the distal tips 22, 28 or on side surfaces thereof. For example, FIGS. 2A and 2C illustrate exemplary distal tips with openings at the end of the distal tip, and FIG. 2B illustrates an exemplary distal tip with the opening on a side surface thereof. Furthermore, the openings may have the same or differently sized and shaped openings, such as circular (as shown in FIG. 2A), oval (as shown in FIG. 2B), triangular, rectangular, diamond (as shown in FIG. 2C), or other suitable shape.

The distal tips 22, 28 may be formed of a metal or polymeric material, or a combination thereof.

In certain implementations, the steam opening 24 is sized such that a width of the steam exiting the steam opening 24 is within about 1 millimeter of a diameter of the dental implant that is being cleaned intraorally with the dental cleaning device 10. For example, the steam opening 24 may be between about 0.1 and about 1.5 mm in diameter. In addition, during application of the steam, the steam opening 24 may be disposed between about 0.5 and about 5 mm away from the implant surface being cleaned.

The solenoid valve 16 is in electrical communication with the computer processor 18 and is configured for selectively allowing steam to pass through the solenoid valve 16 to the opening 24. In some implementations, the valve 16 is opened and closed intermittently.

In some implementations, the cooling fluid is applied intraorally after application of the steam to prevent the steam from cooking the patient's gum tissue. For example, the cooling fluid may have a temperature of about 98.6° F. or less.

In the implementation shown in FIG. 1, the steamer 14 receives cooling fluid from the cooling fluid reservoir 12 and heats the fluid until it becomes steam. The steam then flows through the solenoid valve 16 and the steam conduit 20 (when the solenoid valve 16 is open) to the distal tip 24. However, in other implementations (not shown), the fluid supplied to the steamer 14 may be from another source that is external to the system 10 or a second reservoir that is part of the system 10. The steam may be pressurized to between about 40 and about 80 psi, according to some implementations.

The solenoid valve 16 is in electrical communication with the computer processor 18, and the computer processor 18 is configured for instructing the solenoid valve 16 to open or close. In addition, the computer processor 18 may be further configured for: (1) receiving a first input requesting that the solenoid valve 16 be opened; (2) causing the solenoid valve 16 to open in response to receiving the first input; (3) receiving a second input requesting that the solenoid valve 16 be closed; and (4) causing the solenoid valve 16 to close in response to receiving the second input.

The first input may be a signal resulting from the depression of a button on the hand piece 32 to which a portion of the steam conduit 20 and the cooling fluid conduit 26 are attached, according to one implementation, or from the depression of a pedal. Alternatively, the first input may be a signal from a timer that is part of the computer processor 18, and the computer processor 18 is configured for generating instructions for the solenoid valve 16 to close after steam has passed through the steam opening 24 for a preset time period. The preset time period for applying the steam may be about 3 seconds, for example. In other implementations, the preset time period may be greater or less than about 3 seconds. In another alternative implementation (not shown), the timer may be separate from the computer processor 18 but in electrical communication therewith.

In certain implementations, the flow of the cooling fluid through the cooling fluid conduit 26 is controlled by the peristaltic pump 34 in electrical communication with the computer processor 18. In such implementations, the computer processor 18 is further configured for: (1) increasing a speed of the peristaltic pump 34 to cause the cooling fluid to flow through the distal end 28 of the cooling fluid conduit 26 immediately after the solenoid valve 16 has closed, and (2) decreasing the speed of the peristaltic pump 34 to cease the cooling fluid from flowing through the distal end 28 of the cooling fluid conduit 26 after the cooling fluid has passed through the cooling fluid opening 30 for a second preset time period. In other implementations, the computer processor 18 may be configured for: (1) increasing a speed of the peristaltic pump 34 to cause the cooling fluid to flow through the cooling fluid opening 30 of the cooling fluid conduit 26 immediately after the solenoid valve 16 has closed, and (2) decreasing the speed of the peristaltic pump 34 to cease the cooling fluid from flowing through the cooling fluid opening 30 of the cooling fluid conduit 26 immediately before the solenoid valve 16 is opened. And, in yet another implementation, the computer processor 18 may be configured for increasing or decreasing the speed of the peristaltic pump 34 after a preset time period. For example, the preset time period may be about 2 seconds after the steam has been applied for about 3 seconds. However, in other implementations, the preset time periods may be greater or less than this example. In other implementations, the flow of cooling fluid may be controlled by a valve or other suitable mechanism.

The device 10 may also be used to apply steam extra orally, such as to sterilize or clean surfaces prior to installation within the patient's body, according to some implementations. For example, the device 10 may be useful for extra orally steaming provisionals, crowns, veneers, and implant componentry.

The terminology used herein is for the purpose of describing particular implementations only and is not intended to be limiting of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various implementations of the present invention has been presented for purposes of illustration and description, but is not intended to be exhaustive or limited to the invention in the form disclosed. Many modifications and variations will be apparent to those of ordinary skill in the art without departing from the scope and spirit of the invention. The implementations were chosen and described to best explain the principles of the invention and the practical application, and to enable others of ordinary skill in the art to understand the invention for various implementations with various modifications as are suited to the particular use contemplated.

The invention claimed is:

1. An intra-oral dental implant surface cleaning device comprising:
   a steamer that heats fluid until the fluid becomes steam;
   a reservoir that holds a cooling fluid;
   a first conduit having a first distal tip, the first distal tip defining a first opening;
   a second conduit having a second distal tip, the second distal tip defining a second opening, the second opening being disposed adjacent the first opening, wherein a diameter of the first opening is sized such that a width of the steam exiting the first opening is adapted to be within 1 mm of a diameter of a dental implant to be sanitized by the steam; and
   a valve in fluid communication with the first conduit and the steamer, wherein the valve selectively allows steam to pass from the steamer to the first opening,
   wherein steam flows from the steamer through the first opening when the valve is open, and a cooling fluid flows from the cooling reservoir through the second opening, the cooling fluid preventing the steam from damaging bodily tissues and bone adjacent the intra-oral dental implant surface.

2. The dental cleaning device of claim 1, wherein the cooling fluid has a temperature of about 98.6° F. or less.

3. The dental cleaning device of claim 1, wherein the diameter of the first opening is between 0.1 and about 1.5 mm.

4. The dental cleaning device of claim 1, wherein the valve is a solenoid valve, the solenoid valve being in electrical communication with a computer processor, and the computer processor being in communication with a memory, wherein the computer processor executes computer-readable instructions stored on the memory, the instructions cause the computer processor to instruct the solenoid valve to open or close.

5. The dental cleaning device of claim 4, wherein the instructions cause the processor to:
   cause the solenoid valve to open in response to receiving a first input from a control device; and
   cause the solenoid valve to close in response to receiving a second input from the control device.

6. The dental cleaning device of claim 5, wherein the control device comprises a timer, and the timer is in electrical communication with the computer processor, and the instructions cause the computer processor to generate instructions for the solenoid valve to close after steam has passed through the first opening for a preset time period.

7. The dental cleaning device of claim 6, wherein flow of the cooling fluid through the second conduit is controlled by a peristaltic pump in electrical communication with the computer processor, and the instructions cause the computer processor to:
   increase a speed of the peristaltic pump to cause the cooling fluid to flow through the second opening immediately after the solenoid valve has closed, and decrease the speed of the peristaltic pump to cease the cooling fluid from flowing through the second opening after the cooling fluid has passed through the second opening for a second preset time period.

8. The dental cleaning device of claim 5, wherein flow of the cooling fluid through the second conduit is controlled by a peristaltic pump in electrical communication with the computer processor, and the instructions cause the computer processor to:
increase a speed of the peristaltic pump to cause the cooling fluid to flow through the second opening of the second conduit immediately after the solenoid valve has closed, and
decrease the speed of the peristaltic pump to cease the cooling fluid from flowing through the second opening of the second conduit immediately before the solenoid valve is opened.

9. The dental cleaning device of claim 4, wherein the solenoid valve is opened and closed intermittently.

10. The dental cleaning device of claim 1, further comprising a hand piece, wherein the first and second distal tips are disposed on the hand piece.

11. The dental cleaning device of claim 10, wherein the first and second distal tips are removably secured to the hand piece.

12. The dental cleaning device of claim 1, wherein the first opening is spaced apart from the dental implant by a distance of 0.5 to 5 mm when the valve is open.

* * * * *